(12) United States Patent
Baust et al.

(10) Patent No.: US 8,439,905 B2
(45) Date of Patent: May 14, 2013

(54) NUCLEATION ENHANCED SURFACE MODIFICATION TO SUPPORT PHYSICAL VAPOR DEPOSITION TO CREATE A VACUUM

(75) Inventors: John M. Baust, Owego, NY (US); John G. Baust, Owego, NY (US); Roy Cheeks, Harper's Ferry, WV (US); Anthony Robilotto, Binghamton, NY (US); Kristi Snyder, Candor, NY (US)

(73) Assignee: Endocare, Inc., Chadds Ford, PA (US)

( * ) Notice: Subject to any disclaimer, the term of this patent is extended or adjusted under 35 U.S.C. 154(b) by 699 days.

(21) Appl. No.: 12/562,301

(22) Filed: Sep. 18, 2009

(65) Prior Publication Data

US 2010/0076421 A1   Mar. 25, 2010

Related U.S. Application Data

(60) Provisional application No. 61/098,244, filed on Sep. 19, 2008.

(51) Int. Cl.
*A61B 18/02* (2006.01)

(52) U.S. Cl.
USPC ............................................. 606/21

(58) Field of Classification Search ............... 606/20–26
See application file for complete search history.

(56) References Cited

U.S. PATENT DOCUMENTS

| | | | |
|---|---|---|---|
| 3,858,805 A * | 1/1975 | Shen et al. ..................... 239/2.1 |
| 3,971,383 A | 7/1976 | van Gerven | |
| 4,082,096 A | 4/1978 | Benson | |
| 4,243,619 A * | 1/1981 | Fraser et al. ................. 264/40.6 |
| 4,831,846 A | 5/1989 | Sungaila | |
| 5,078,713 A * | 1/1992 | Varney ............................ 606/23 |
| 5,254,116 A * | 10/1993 | Baust et al. ..................... 606/23 |
| 5,400,602 A * | 3/1995 | Chang et al. ................... 62/50.7 |
| 5,423,807 A | 6/1995 | Milder | |
| 5,452,582 A | 9/1995 | Longsworth | |
| 5,520,682 A | 5/1996 | Baust et al. | |
| 5,674,218 A | 10/1997 | Rubinsky et al. | |
| 5,733,280 A | 3/1998 | Avitall | |
| 5,817,326 A * | 10/1998 | Nastasi et al. ................. 424/426 |
| 5,869,604 A * | 2/1999 | Rousseau et al. ............. 530/344 |

(Continued)

OTHER PUBLICATIONS

Fladerer et al. "Homogenous nucleation and droplet growth in supersaturated argon vapor: The cryogenic nucleation pulse chamber," Journal of Chemical Physics (2006), vol. 124. 2006 American Institute of Physics. USA.

*Primary Examiner* — Michael Peffley
*Assistant Examiner* — Daniel Fowler
(74) *Attorney, Agent, or Firm* — Pepper Hamilton LLP

(57) ABSTRACT

The device of the invention takes the form of a catheter/probe and is a closed loop system in which cryogen is delivered along the length of the catheter/probe to the tip where freezing occurs, and then recirculated. The device is a tube within a tube and comprises a number of parts including supply and return (internal) tubes, outer sheath (external tube) seaJed to the inner tubes at one or both ends with a gas filled lumen between the internal and external tubes. The lumen of the external tube is filled with a saturated gas which solidifies upon cooling, thereby creating a vacuum along the catheter length and providing for insulation between the inner and outer tubes, and preventing freezing along the probe shaft length. The outside surface of the internal tubes is modified to potentiate gas nucleation on the outer surfaces of the internal tubes when cooled.

23 Claims, 7 Drawing Sheets

U.S. PATENT DOCUMENTS

| | | | |
|---|---|---|---|
| 5,899,898 A * | 5/1999 | Arless et al. ............ 606/22 |
| 5,951,546 A | 9/1999 | Lorentzen |
| 6,241,722 B1 * | 6/2001 | Dobak et al. ............ 606/23 |
| 6,468,268 B1 | 10/2002 | Abboud et al. |
| 6,468,269 B1 | 10/2002 | Korpan et al. |
| 6,485,560 B1 * | 11/2002 | Scherer et al. ............ 106/672 |
| 6,508,814 B2 | 1/2003 | Tortal et al. |
| 6,547,784 B1 | 4/2003 | Thompson et al. |
| 6,551,309 B1 | 4/2003 | LePivert |
| 6,648,879 B2 | 11/2003 | Joye et al. |
| 6,875,209 B2 | 4/2005 | Zvuloni et al. |
| 6,887,234 B2 | 5/2005 | Abboud et al. |
| 7,156,840 B2 | 1/2007 | Lentz et al. |
| 7,163,535 B2 | 1/2007 | Ryba et al. |
| 7,306,589 B2 | 12/2007 | Swanson |
| 7,306,590 B2 | 12/2007 | Swanson |
| 7,404,816 B2 | 7/2008 | Abboud et al. |
| 2004/0215295 A1 | 10/2004 | Littrup et al. |
| 2006/0079867 A1 | 4/2006 | Berzak et al. |
| 2006/0235375 A1 | 10/2006 | Littrup et al. |
| 2007/0244474 A1 | 10/2007 | DeLonzor et al. |
| 2007/0277550 A1 | 12/2007 | Li et al. |
| 2008/0009845 A1 | 1/2008 | Duong et al. |
| 2008/0027422 A1 | 1/2008 | Vancelette et al. |
| 2008/0147056 A1 | 6/2008 | van der Weide et al. |
| 2008/0173028 A1 | 7/2008 | Littrup et al. |
| 2008/0255551 A1 | 10/2008 | DeLonzor |
| 2008/0300584 A1 | 12/2008 | Lentz et al. |
| 2009/0281533 A1 | 11/2009 | Ingle et al. |
| 2009/0318913 A1 | 12/2009 | Li |
| 2010/0241112 A1 | 9/2010 | Watson |

* cited by examiner

NUCLEATION ENHANCED SURFACE MODIFICATION TO SUPPORT PHYSICAL VAPOR DEPOSITION TO CREATE A VACUUM

RELATED APPLICATIONS

The present application claims priority to U.S. Provisional Patent Application Ser. No. 61/098,244 filed on Sep. 19, 2008 and titled Nucleation Enhanced Surface Modification to Support Physical Vapor Deposition to Create a Vacuum, which is incorporated herein by reference in its entirety.

FIELD OF THE INVENTION

The present invention relates generally to the medical technology field and, in particular, to a medical device for use in a cryogenic system.

BACKGROUND OF THE INVENTION

Over a recent number of years, there has been a strong movement within the surgical community toward minimally invasive therapies. The main goals of the minimally invasive therapies include: 1) eradication of tissue, 2) decreased hospitalization time, 3) limited postoperative morbidities, 4) shortened return interval to daily functions and work, and 5) reduced overall treatment cost. Cryotherapy is a minimally invasive method of treating a disease state through tissue freezing with thousands of patients now receiving the procedure annually. Currently, cryotherapy is used to treat numerous disease states including organ confined tumors such as prostate, kidney, liver, as well as cardiovascular disease, retinal detachment, pain management, and other illness/disease states.

Cryotherapy is an effective yet minimally invasive alternative to surgery and radiation therapy. The procedure is done under either general or epidural anesthesia. Since it is minimally invasive, it offers patients a quicker recovery and reduced severity of potential side effects. Without the expense associated with major surgery or an extended hospital stay, cryotherapy is a cost-effective treatment option.

Prior studies have utilized various cryosurgical probes and procedures for insulating and delivering cryogen without excess freezing of tissue along the shaft of the cryoprobe. These processes include permanent vacuums or insulation along the length of the probe. Thus, there exists a need for improvements in cryotherapy, and medical devices or components associated with the treatment to better circulate liquid cryogen to a cryoprobe and facilitate improved measures for treatment and cost.

The medical device of the invention disclosed herein will accommodate the needs for improved cryoprobes and catheters as utilized in cardiac care, cancer therapeutics, and cryotreatment of other disease states. The invention will allow for temperature induced transient vacuum insulation of the shaft of a cryoprobe or catheter. Embodiments of the device will also allow for the enhanced deposition on the outer surfaces of the inner tubes through modification of the tube surfaces, and thereby contribute to the insulation barrier. The invention will facilitate the eradication of tissue, decrease hospitalization time, limit postoperative morbidities, shorten return to daily functions and work, and further reduce the overall treatment cost. In addition, these improvements to device design and application will increase its utilization for the treatment of multiple disease states in various fields of health care and surgical applications, including cardiac care, cancer treatment, neuro/electrophysiology, and numerous others.

SUMMARY OF THE INVENTION

The following invention is a cryogenic medical device/product designed to deliver subcooled liquid cryogen to various configurations of cryoprobes for the treatment of damaged, diseased, cancerous or other unwanted tissues. The device is a closed/semi-closed system in which the liquid cryogen is contained in both the supply and return stages.

The product for performing cryotherapeutic procedures is selected from a group comprising catheters, probes, cryo-instruments, probing rods, and cryo-devices. The product comprises a support structure as a longitudinal body which comprises a proximal end and a distal end with a tubular shaft positioned therebetween, the tubular shaft comprising a lumen therein, and the support structure having an outer sheath defining the dimension and shape of the longitudinal body. A connector positioned at the proximal end is capable of sealing to the outer sheath. At least one first internal tube and at least one second internal tube protrude into the lumen of the longitudinal body through the connector; the first internal tube providing a supply line for cryogen to pass to the distal end and the second internal tube providing a return line for cryogen to pass from the distal end. An insulative vacuum is created within the lumen of the longitudinal body along a defined length of the tubular shaft. The insulative vacuum may run the entire length of the tubular shaft or the longitudinal body, or any portion thereof.

In one embodiment of the invention, a cryogenic catheter or probe designed to deliver cryogen (liquid or gas) for the treatment of damaged, diseased, cancerous or other unwanted tissues is disclosed. This medical device has been preliminarily designated as the "Self Actuated Vacuum Cryogenic Catheter" concept. The "Self Actuated Vacuum Cryogenic Catheter" is a closed loop system in which the cryogen is transported through its length to the tip where freezing occurs, and then recirculated to a cryogenic delivery system. The product/device is a tube within a tube and comprises a number of parts including a supply and return tubes (i.e. internal tubes), outer sheath (i.e. external tube) sealed to the inner tubes at one or both ends with a gas filled lumen between the internal and external tubes. The lumen of the external tube is filled with a non-equilibrating saturated gas which solidifies upon cooling, thereby creating a vacuum along the length of the catheter to provide for insulation between the inner and outer tubes and preventing freezing along the length of the probe shaft. Further the outside surface of the internal tubes is modified to potentiate gas nucleation on the outer surface of the internal tubes upon cooling.

At the distal end or tip of the probe shaft, the internal tubes come into contact with the outer tube and create a defined region of ultra cold temperatures to cool and freeze the target tissue region. The catheter is designed to carry liquid cryogen under various pressures as well as liquid cryogens of varying temperatures. Delivery of cryogen to the catheter is provided by a cryogenic medical device console through the connection of the longitudinal body.

In one embodiment, a dual insulative barrier is capable of being formed. In one aspect, the device creates a temperature initiated transient vacuum insulation along the length of a catheter. The device further couples the temperature initiated vacuum with that of a surface modification along the inner tubes/lines to enhance nucleation and deposition of the saturated gas on the outer surface of the inner tubes to create an additional layer of insulation. The enhanced deposition or nucleation modification contributes by making the vacuum more effective. In addition, the saturated gas filled lumen of the outer tube at ambient temperature may be run at any given pressure. For exemplary purposes and not limitation, one embodiment maintains the pressure at atmospheric levels or may control the pressure to elevated or reduced levels.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion. Further, the below representations of a longitudinal body may not be drawn to scale where particular aspects extend the longitudinal body to lengths up to six feet and beyond (as dependent on the desired application).

DETAILED DESCRIPTION

Figure 1A:
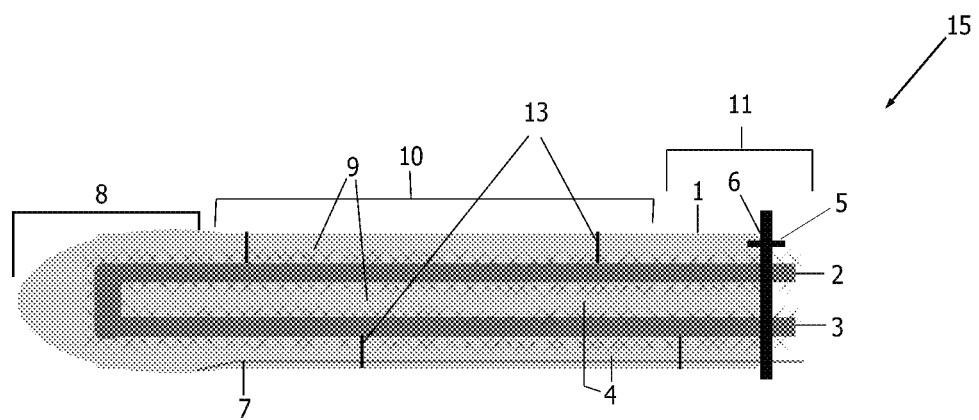
FIG. 1A is a side view of an illustrative embodiment of the device of the disclosed invention when the lumen is filled with particles in gaseous state.

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

An external view of a device 15 in accordance with one embodiment of the present invention is shown in FIG. 1 and FIG. 2. The device 15 of an embodiment takes the form of a catheter 15 having a tube within a tube configuration, and forming the longitudinal body 15. The longitudinal body 15 comprises internal tubes, including a supply line 2 and a return line 3, contained within an outer insulation tube 1 and continuously running through the length of the tubular shaft 10 of the longitudinal body 15. The outer insulation tube 1, or outer catheter sheath 1, defines the size, shape, and dimensions of the longitudinal body 15 which conforms to dimensions that are capable of housing the internal lines 2, 3. The tubular shaft therefore extends from a proximal end 11 of the longitudinal body 15 to a distal end or tip 8. The outer catheter sheath 1 provides a unitary support structure for the flow of liquid cryogen to and from the distal end of the catheter tip 8; desirably, the distal end is where a freezing event is initiated. The liquid cryogen utilized in one embodiment may be liquid nitrogen, though any desired liquid cryogen may be utilized and the system adjusted to accommodate for different chemistries.

The inner supply line 2 and return line 3 are maintained in the center of the outer sheath 1 by open configuration insulative spacers 13 placed throughout the catheter 15. The open configuration allows for a catheter lumen 4 to be filled with gas. The outer catheter sheath 1 is sealed to the connector 6 to create the gaseous lumen 4. The tip 8, in combination with the inner supply line 2 and the return line 3 come into contact with the outer sheath 1 at the distal end to develop a freezing region.

In addition, in one embodiment, the shaft 10 of the catheter 15 is flexible, as facilitated by a deflection wire 7 that runs along the shaft 10, the shaft of which is insulated by a temperature induced vacuum. The deflection wire 7 is a control line that runs down the shaft 10 to the tip of the catheter 15 to allow the catheter tip 8 to be moved on an angle, in a finger-like motion to steer and direct the catheter/probe 15 to the target tissue. In one embodiment, the deflection wire 7 guides the device 15 and monitors environmental measures of temperature, pressure, and/or physiological conditions. The guide 7 may integrate individual components and sensors such as an optical imaging component in connection with the guide or any number of thermocouples, pressure transducers, electrocardiogram monitors, or other electrophysiological sensors, alone or in combination.

Another embodiment of the present invention may use insulative foam (e.g. styrofoam, plastics, rubberized materials or other such insulative compositions) to separate the outer shaft 10 from the internal lines 2, 3 (i.e. inner supply line 2 and return line 3). Various aspects of the invention, however, accommodate a catheter tip 8 as designed to be steerable and deflectable to allow for guided targeting to the desired tissue site. In one aspect, spacers or insulative foam may be utilized to prevent internal supply and return lines from contacting the outer sheath. In another aspect, any freeze zone can be produced as designated by the configurations of catheter tips 8. (See FIGS. 3-6).

In the process of utilizing the catheter 15 of the present invention, a condensation based vacuum insulation is temperature dependent and located in the catheter 15. Upon the outer surfaces 9 of the walls of the supply line 2 and return line 3, a process of physically marking or chemically etching the surfaces 9 enhances nucleation and physical vaporization deposition of saturated gas. For exemplary purposes only and not limitation, the surface may be roughened, sprayed with any number of powder-like substances like silica, metallic particles and/or a carbon coating. The lumen 4 within the outer sheath 1 is filled with select vapors, or non-equilibrated phase change gas 14. In this embodiment, for example, butane is utilized which remains in a gaseous state at about room temperature, between about 0° C. to about 37° C. (See FIGS. 1A, 1B), but solidifies into crystalline deposits 12 upon chilling to below about 0° C., and simultaneously deposits a film of crystals in a controlled deposition process upon the designated surfaces 9 (See FIGS. 2A, 2B). It should be noted, however, that the temperature variations are dependent upon the type of vapors utilized, chemical characteristics and variations of vapor combinations. Therefore, temperatures of varying gases may be selectively controlled so as to create the same or similar effect of spontaneous nucleation and simultaneous deposition upon reaching a freezing temperature.

Figure 2A:
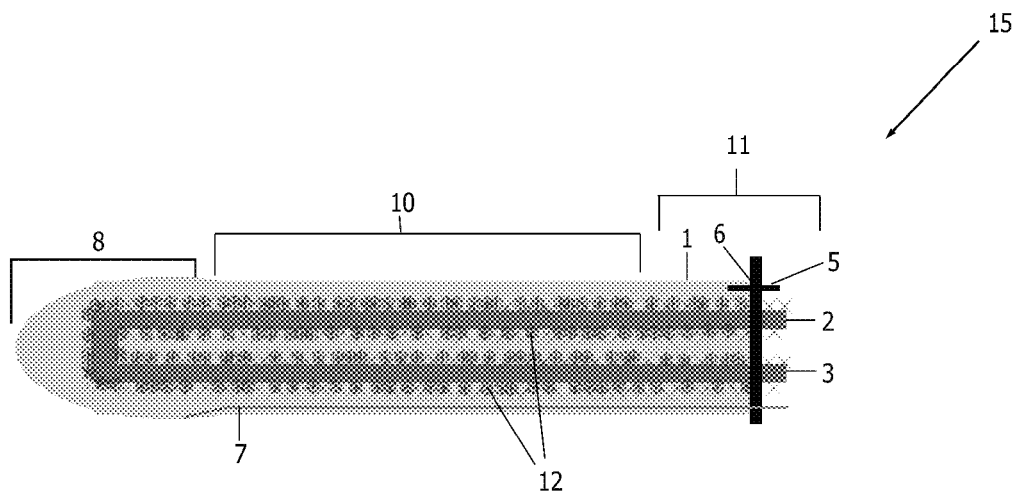
FIG. 2A is a side view of an illustrative embodiment of the device of the disclosed invention as temperatures are reduced to a freezing point of the particular gas selected.

In addition, one embodiment may interconnect a vacuum line of a cryosystem console with the catheter or probe 15 through a vacuum port 5 of the connector 6 as illustrated in FIGS. 1A and 2A. In one aspect, the vacuum is formed upon sealing the lumen at the connector and mechanically drawing a vacuum through vacuum port 5. In another aspect, the vacuum port may connect via its own vacuum system or in combination with the vacuum pump of the cryosystem. Thus, a dual insulative barrier can be created in the present invention by either a mechanically drawn vacuum or a spontaneously induced vacuum [via temperature inducement] (the vacuum itself creating the insulation for the internal tubes) in combination with a nucleation enhanced surface modification to enhance deposition of gas crystals onto the designated outer surfaces of the internal tubes. Desirably, the outer walls of the internal tubes are physically or chemically etched at designated sites along the tubular shaft. A region within the distal end or tip 8 can then be configured specifically designated freeze zones.

Figure 1B:
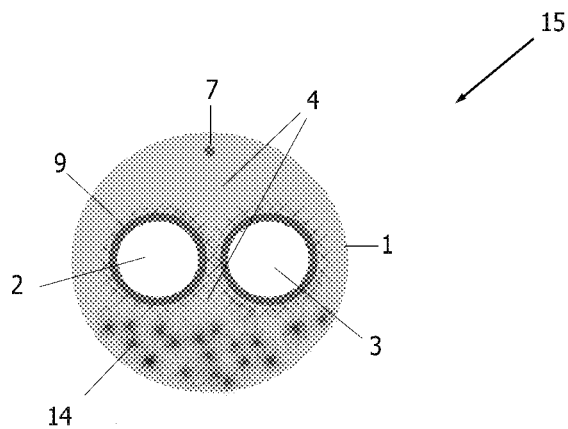
FIG. 1B is a cross-sectional view of the illustrative embodiment in FIG. 1A.
Figure 2B:
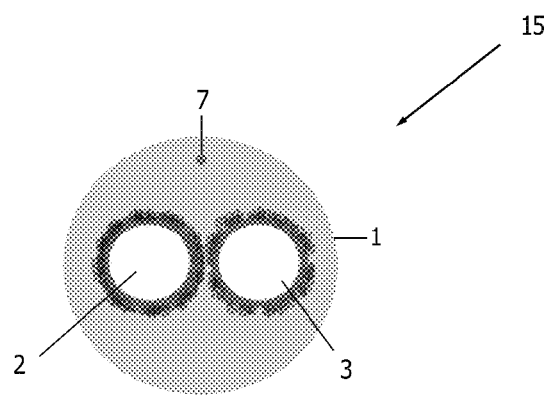
FIG. 2B is a cross-sectional view of the illustrative embodiment in FIG. 2A.
Figure 3:
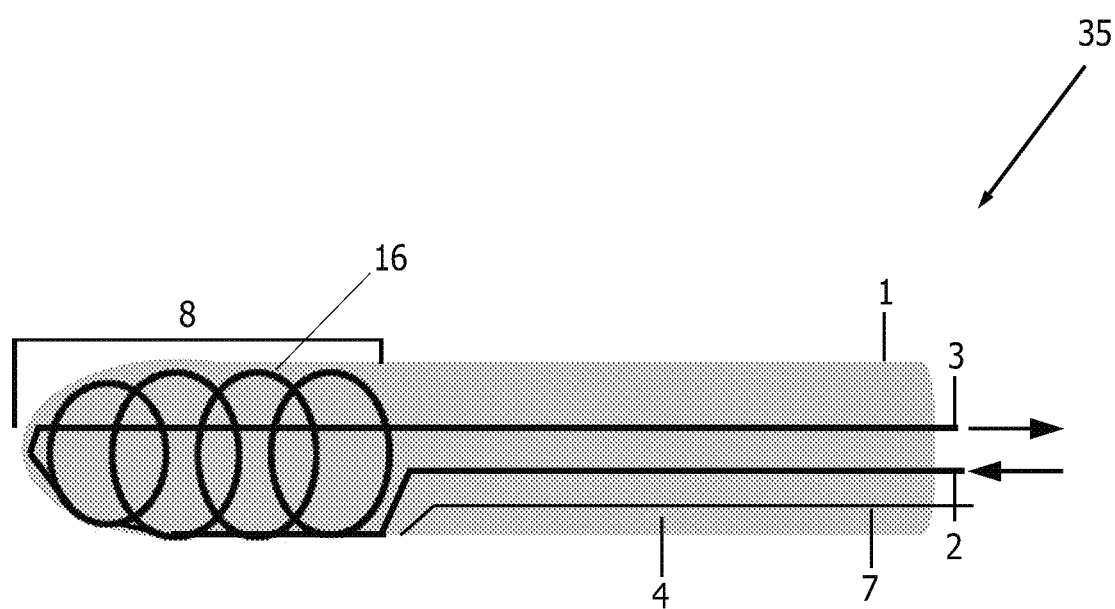
FIGS. 3-6 are side views of various embodiments of a device of the invention.

In the described embodiments, nucleation/sublimation in combination with a deposition process forms solid crystals along the supply line 2 and return line 3 outer walls, and spontaneously results in an evacuated space between the inner line 2 and the outer line 3. The evacuated space acts as an insulative barrier between the outer catheter sheath and the frost encased inner lines 2, 3. Film wise deposition along an entire surface of the supply line 2 and return line 3 results in crystalline film deposits of low thermal conductivity (Note: The 'x' marks in FIGS. 1A and 1B demonstrate the nucleation enriched supply and return tubular surfaces 9, the tubular surfaces of which are modified by processes described herein. The non-solidified gas crystals 14, non-equilibrating phase change gas particles 14, are illustrated in FIG. 1B. Nucleated or solidified particles, as designated by "*" are depicted in FIGS. 2A, 2B upon the modifications "x" (etching) on the surfaces 9. The nucleated particles 12 (marked as "*") are formed when the gas reaches a freezing temperature. In one aspect, any pressure may be utilized. For exemplary purposes and not limitation, pressure in the device may be maintained or controllably elevated or reduced. For instance, gas may be maintained at atmospheric or high pressure to support the retention of the vapor state at room temperature.

Other aspects of embodiments of the present invention include gas as either a pure component or as a mixture of various components. Such gaseous compositions, for exemplary purposes only and not limitation, may comprise butane, carbon dioxide, iodine, camphor, and/or nitrous oxide.

In another embodiment, an enhanced nucleation surface 9 on inner tube/line 2, 3 surfaces may result where a process includes treating the walls of the inner lines 2, 3 to match nucleating efficiency with the chemical characteristics of the gas to be deposited (e.g. marking the surfaces with impurities, utilizing silica, or other powderized material, chemically coating or etching) and thereby create a similar effect.

Embodiments of the present invention manipulate the structural configurations of the tips 8, as illustrated in FIGS. 3-6. In one or more embodiments depicted, the freeze zone is created where the internal components 2/3 contact the outer sheath 1 at a distal end 8. One such embodiment in FIG. 3 includes a closed loop coiled supply tube 16 in contact with the outer sheath 1 to affect a cold sink. The supply line 2 and return line 3 convene at the freezing zone of the tip in the formation of a coil 16.

Figure 4:
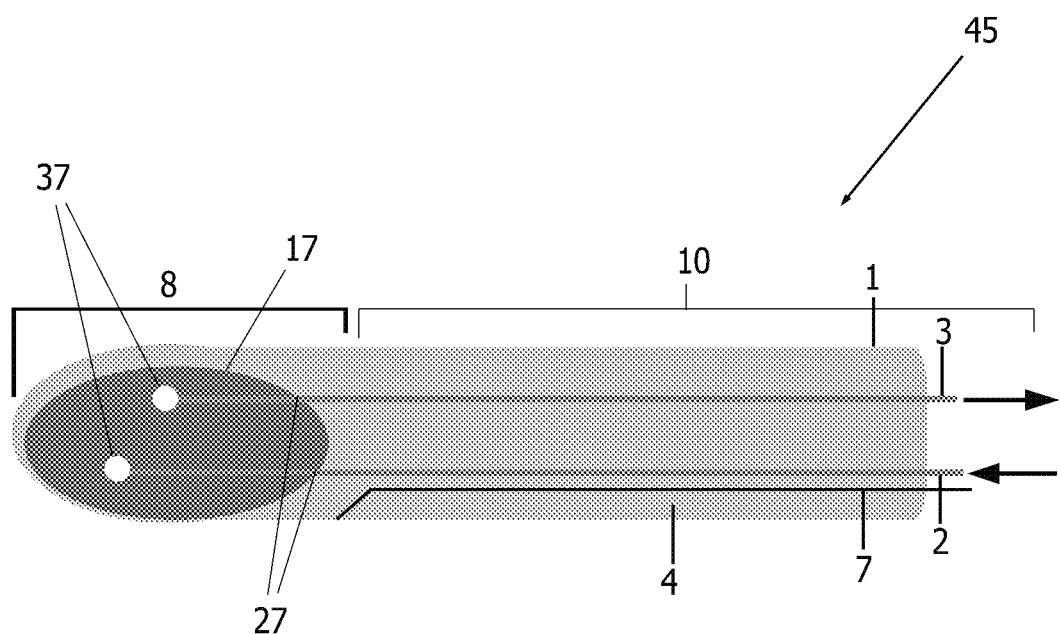

In another embodiment, as shown in FIG. 4, a metallic balloon tip 17 is illustrated in which cryogen is circulated in the tip and then returned. The supply line 2 extends to a distance into the tip 8 beyond the extension of return line 3 such that cryogen pumped into the balloon-like tip 7 circulates within the sealed confines of the inflated region when the catheter is engaged for the procedure. The supply line 2, however, can extend any length or distance into the tip. The balloon-like tip may be composed of any flexible or rigid material including metallic, plastic, or ceramic compositions. Similarly, the balloon-like structure within the sheath may cause the outer sheath 1 to inflate and deflate for cryogenic procedures. For example, and not limitation, cryogenic procedures performed within a vessel may advantageously make use of an inflatable cryogenic element 17 at the distal end of the probe so that the outer sheath expands as the internal inflatable cryogenic element expands.

Also depicted in FIG. 4, the inflatable tip is a sealed within the distal tip 8 in connection with both an individual supply line 2 and an individual return line 3. The needle-like probe 45 is a longitudinal tube 45 having a distal end 8 which serves as the freezing region in connection with the tubular shaft 10 (only a portion of which is illustrated here in FIG. 4). A sealed interface 27 ensures that the inflatable area can expand and contract in correspondence with the fill and removal of the cryogenic medium. The cryogenic medium in one embodiment in liquid nitrogen. Any cryogen may be utilized, however, to accommodate the demands of the system and treatment measures. Further, the inflatable structure, here, a metallic balloon tip, is designed and configured with materials that conform to the use of liquid nitrogen. Without considering the type of cryogen utilized, the inflatable tip may rupture or create undesired effects. For exemplary purposes, and not limitation, the tip of the present embodiment is designed to meet the needs of a system and device utilizing liquid nitrogen.

Another aspect of the probe/system in FIG. 4 is that the sealed interface 27 may be a wall or connection component (not illustrated) which seals the freezing region 8 of the tip away from the tubular shaft 10 in a blunt-tip probe. The sealed interface allows a supply line 2 and a return line 3 to access the freezing tip, the open ends 37 of which allow cryogen to be dispersed within the sealed zone 8. In FIG. 4, the sealed zone is the balloon tip, but any size or shape of sealed zone may be utilized in different aspects of the present invention to create similar results. It should be noted that the open-ended supply line in one embodiment extends further into the sealed zone toward the distal end and beyond the open end of the return line. Any length of supply line or return line, however, may be utilized; the lengths may be designed having equal lengths or different lengths, as desired.

Figure 5:
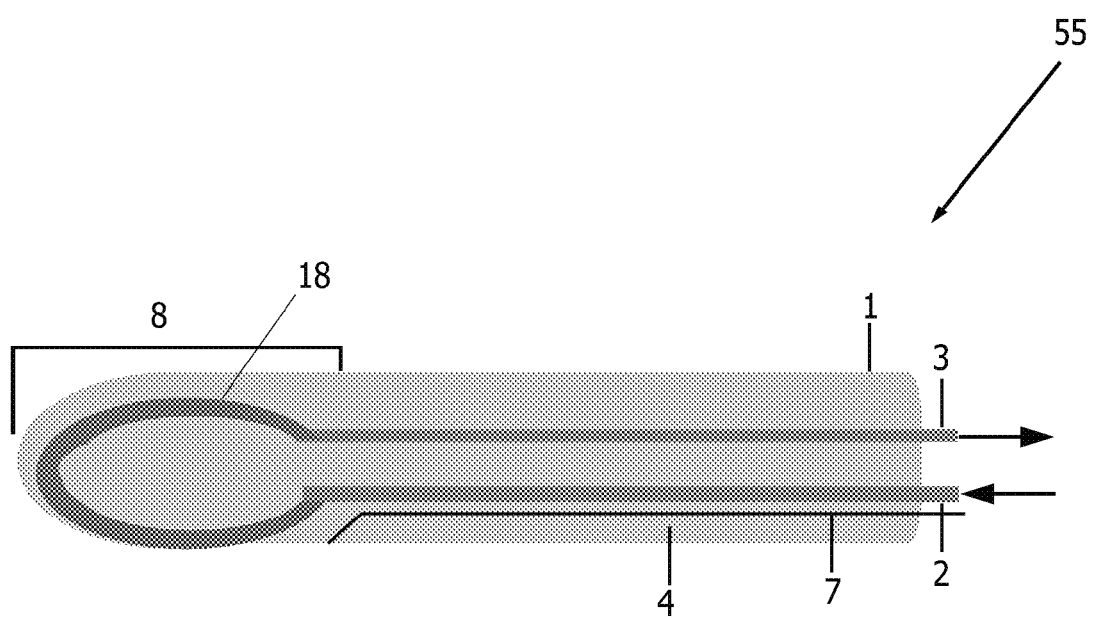

FIG. 5 is another embodiment of the probe tip which illustrates a closed loop tip 18. The closed loop tip integrally connects both supply line 2 and return line 3 to form a unitary structure for delivery and return of liquid cryogen to the distal end in the freezing region of the probe.

Figure 6:
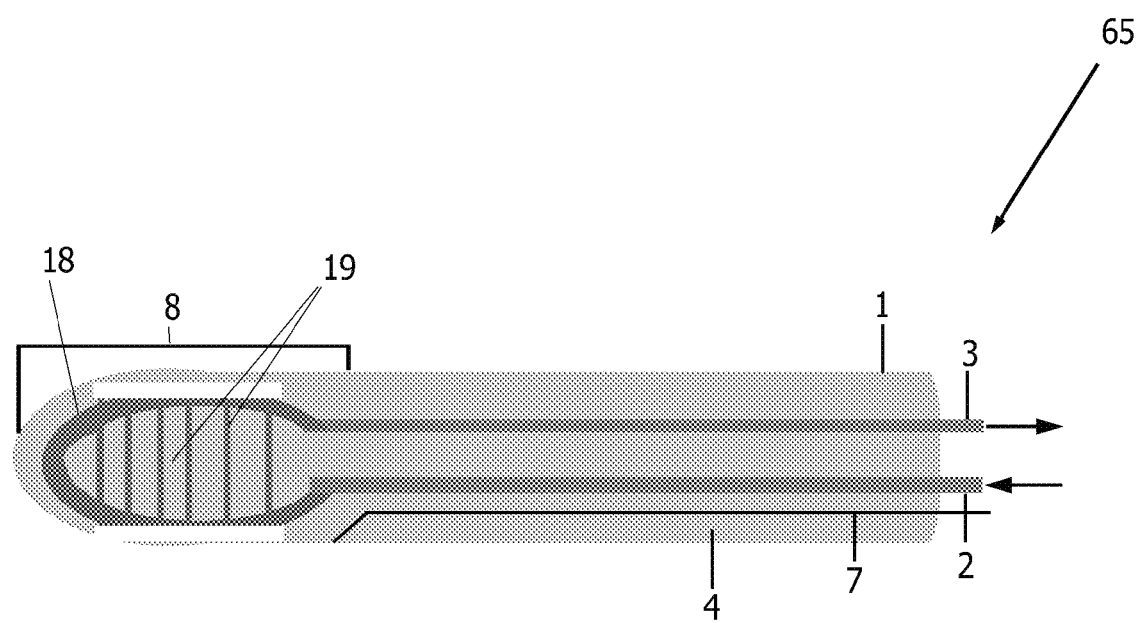

FIG. 6 illustrates a cryoprobe 65 as a closed loop tip with a finned heat exchanger 19 within the freezing zone or tip 8. The heat exchanger provides for a more efficient heat extraction from the tissue, thereby providing faster cryotreatment and greater injury/freezing to the tissue site. The heat exchanger is also utilized to cool the cryogen prior to return to the console, resulting in increased cryogen recovery. Other variations in tip design may be any size and dimension or take the size or shape of known catheters 15 in the field. Further configurations of the cryoprobe as described infra may also accommodate other structural variations.

Figure 7:
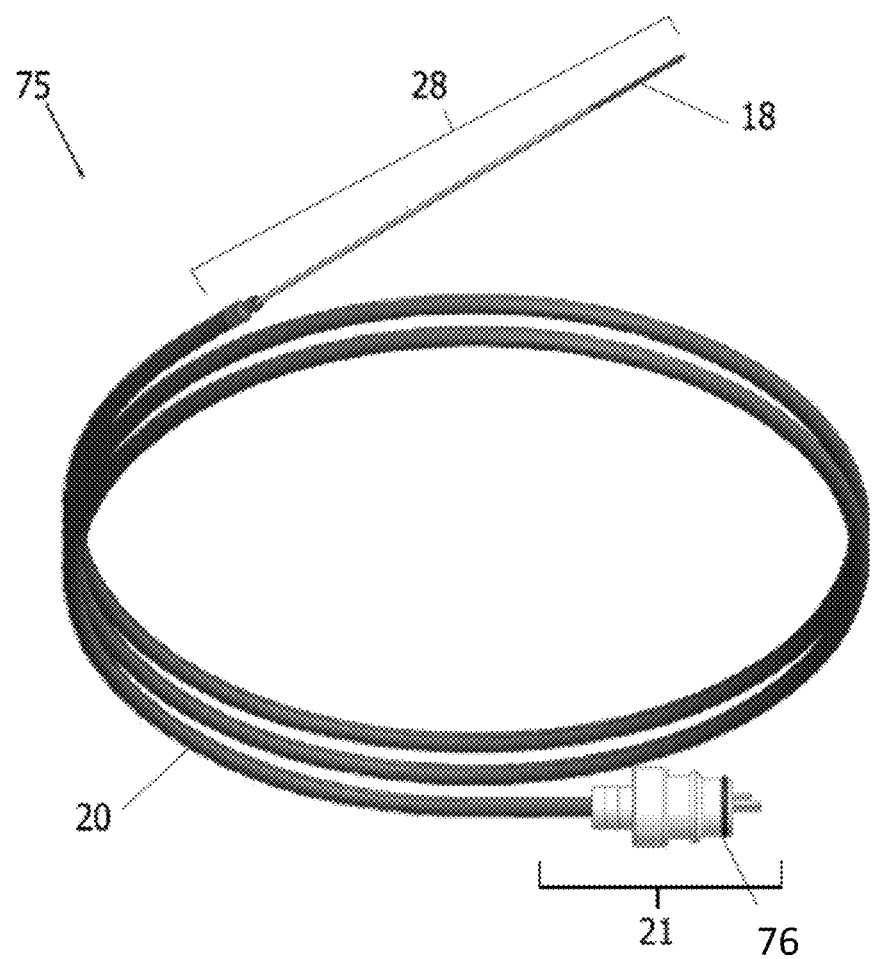
FIG. 7 is an illustrative embodiment of a product of the present invention.

As demonstrated in FIG. 7, the product for performing cryotherapeutic procedures is illustrated as an elongated body 75, about six feet in length. A connector 76 at a proximal end 21 allows the cryoprobe to be connected with a cryogenic delivery system. The freezing region, or tip 18 is positioned within the distal end 28 with a flexible tubular shaft 20 positioned between the ends. Some of the various embodiments of distal end 28 have been depicted in FIGS. 3-6, embodiments of distal ends 35, 45, 55, 65 which can serve as replacements for the distal end 28 within the elongated product 75. The support structure 75 comprises an outer sheath (as illustrated in FIGS. 1 and 2) which has at least one internal tube configured inside the sheath to deliver and return liquid cryogen to and from the freezing region/zone at the target tissue site. When in use and hooked to a cryogenic delivery system, the product 75 simultaneously produces an insulative vacuum throughout the tubular shaft 20. A dual insulative barrier is formed by a temperature initiated transient vacuum in combination with an enhanced nucleation deposition process along the outer surface of the internal tubes (discussed infra). The nucleation sites are therefore capable of selective placement anywhere throughout the product.

In one embodiment, the distal end 28 is a needle-like probe end. In another embodiment, the distal end 28 takes the form of a blunt-tip probe end. The distal portion 28 may be integral with the tubular shaft or be removably placed in connection therewith. The interconnections of proximal connector, tubular shaft, and distal probe ends thus determines whether or not the individual parts, alone or in combination, may be reused, or disposed of. Further, the length of the distal end 28 may vary according to treatment procedure and may be any size, shape and dimension to correspond to the tissue treated.

In utilizing the medical device of the present invention, various methods in the industry may be employed in accordance with accepted cryogenic applications. As discussed, the embodiments of the present invention are for exemplary purposes only and not limitation. Advantageously, this device can be utilized for targeted thermal therapies. Various cryosurgical devices and procedures to apply freezing temperatures to a target tissue may be employed for use with the medical device of the invention. The medical device further has been developed to enable and improve the approaches used to target or ablate tissue.

As disclosed herein, the device in the invention may be of any size, shape, or dimension. The device may be single use disposable or a multi-use/reusable part (and capable of being sterilized between individual patient treatments). In one embodiment, the longitudinal body extends up to about 6-8 feet or more. Any length, however, may be utilized as designed for particular therapies and treatments. Dimensions less than 12 inches, however, may also be better suited where attached tubing, removable, detachable, or disposable parts are integrated in the design.

In one aspect, the entire longitudinal body may incorporate the nucleation enhanced sites on any outer surface of the internal tubes or on any other designated area or specified site within the lumen of the body. In another aspect, the tubular shaft comprises nucleation sites along the outer surfaces of the internal tubes, thereby reserving the distal end as the freeze zone for positioning with the targeted tissue.

Thus, the invention facilitates other improvements in cryotherapy, and medical devices or components associated with the treatment. The medical device of the invention allows for the circulation (cooling, delivery, and return) of liquid cryogen to a cryoprobe for the freezing of targeted tissue. The invention facilitates the eradication of tissue and can thereby decrease hospitalization time; further advantages reduce postoperative morbidities, shorten return to daily functions and work, and further lessen the overall treatment cost. These improvements to device design and application can also increase utilization of the device for the treatment of multiple disease states.

The device of the invention represents an approach in the development of cryosurgical devices by allowing for temperature induced transient vacuum insulation along the shaft of a cryoprobe or catheter; including insulating the shaft of a cryoprobe or catheter and delivery of cryogen in targeted thermal therapy. Furthermore, the device has been developed to couple the temperature initiated vacuum with that of a surface modification along the inner tubes to enable enhanced nucleation and deposition of the saturated gas on the surface of the inner tubes and create an additional layer of insulation. In one aspect, the device of the invention allows for the enhanced deposition on the outer surface of the inner tubes through modification of the tube surface, thereby creating an additional insulation barrier. In another aspect, the saturated gas filled lumen of the outer tube at ambient temperature may be either elevated or at atmospheric pressure.

The embodiments of the present invention may be modified to take the shape of any device, container, apparatus, or vessel currently used in industry. Specifically, cylindrical or alternative structural designs may be utilized in the cryogenic system for improved catheter/probe access to a tissue target. Further, any rearrangement of the tubes/lines in combination with the components of the above system may take many forms and be of any size, shape, or passageway.

As presented, the multiple embodiments of the present invention offer several improvements over standard medical devices currently used in cryogenic industry. The improved cryogenic medical devices remarkably enhance its utilization for the cooling, delivery and return of a liquid cryogen to a cryoprobe for the freezing of targeted tissue. The previously unforeseen benefits have been realized and conveniently offer advantages for the treatment of multiple disease states. In addition, the improvements enable construction of the device as designed to enable easy handling, storage, and accessibility.

As exemplified, the device may include any unitary structure or device with the capacity to integrally incorporate any combination of such structures. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A product for performing cryotherapeutic procedures, selected from a group comprising catheters, probes, cryo-instruments, probing rods, and cryo-devices, said product comprising:
   a longitudinal body which comprises
      a proximal end and
      a distal end with
      a tubular shaft positioned therebetween,
   said longitudinal body comprising a lumen therein, and
   said longitudinal body having an outer sheath defining the dimension and shape of said longitudinal body;
   a connector positioned at said proximal end and capable of sealing to said outer sheath;
   at least one first internal tube and at least one second internal tube protruding into said lumen of said longitudinal body through said connector;
   said first internal tube providing a supply line for cryogen to pass to said distal end and said second internal tube providing a return line for cryogen to pass from said distal end; and
   an insulative vacuum is created within said lumen of said longitudinal body along a length of said distal end of the longitudinal body;
   wherein outer surfaces of one or more internal tubes comprise a nucleation enhanced surface modification that promotes a physical deposition of a saturated gas onto said outer surfaces to facilitate formation of said insulative vacuum.

2. The product of claim 1, wherein said insulative vacuum is formed from a non-equilibrating phase change gas.

3. The product of claim 2, wherein said insulative vacuum is spontaneously induced when said product is utilized in cryotherapeutic procedures.

4. The product of claim 2, wherein said insulative vacuum is dependent on temperature reduction of said non-equilibrating phase change gas, said non-equilibrating phase change gas precipitating out of said lumen and solidifying upon said outer surfaces of said internal tubes.

5. The product of claim 1, wherein the nucleation enhanced surface modification of said outer surfaces of one or more internal tubes is produced by a process that includes treating said outer surfaces of said one or more internal tubes to match nucleating efficiency with chemical characteristics of the non-equilibrating phase change gas.

6. The product of claim 5, wherein the nucleation enhanced surface modification of said outer surfaces is produced by a process that includes treating said outer surfaces to match nucleating efficiency with chemical characteristics of the non-equilibrating phase change gas, said process selected from the group consisting of: marking the outer surfaces with impurities, chemically coating the outer surfaces and etching the outer surfaces.

7. The product of claim 1, wherein said first internal tube and said second internal tube form a unitary tubular structure which circulates a cryogenic medium to and from said distal end of said longitudinal body.

8. The product of claim 7, wherein said unitary tubular structure contacts said outer sheath to form a freezing region.

9. The product of claim 8, wherein said unitary tubular structure contacts said outer sheath at said distal end.

10. The product of claim 1, wherein said first and second internal tubes form a closed loop tip at a distal end of said longitudinal body.

11. The product of claim 10, wherein said closed loop tip comprises a heat exchanger within said longitudinal body.

12. The product of claim 10, wherein said closed loop tip is a closed loop coil.

13. The product of claim 1, further comprising one or more sealed interfaces which isolate said freezing zone.

14. The product of claim 13, wherein said one or more sealed interfaces permits at least one said supply line and at least one said return line to circulate cryogen through to said distal end.

15. The product of claim 14, wherein said one or more sealed interfaces is a wall which connects to said outer sheath and seals said freezing zone at a tip of said distal end and away from said tubular shaft.

16. The product of claim 1, further comprising a guide, deflection wire, steering component, or directional element extending through said tubular shaft from said proximal end to a near point of said distal end.

17. The product of claim 1, wherein said longitudinal body comprises at least one of: a monitoring element, a sensor, an optical imaging component, a thermocouple, an electrocardiogram monitor, a pressure transducer or an electrophysiological sensor.

18. The product of claim 1, further comprising a configuration of spacers within said tubular shaft to position said supply line and said return line within said longitudinal body and away from contact with said outer sheath.

19. The product of claim 1, further comprising an insulative foam to separate said outer sheath from said first and second internal tubes.

20. A method of providing an insulated cryogenic instrument, said method comprising the steps of:
providing a product of claim 1;
filling said lumen of said longitudinal body with one or more vapors;
cooling said one or more vapors;
forming nucleated particles in which said one or more vapors from a gaseous state solidify into liquid or crystalline form along said at least one outer surface of said one or more internal tubes; and
forming an evacuated space between said one or more internal tubes and said outer sheath, said evacuated space providing an insulative vacuum within said lumen of said longitudinal body;
wherein said step of cooling and said step of forming nucleated particles takes place simultaneously and spontaneously induces said step of forming an evacuated space.

21. The method of claim 20, wherein said step of cooling said vapors is induced by reducing temperatures to a freezing point which sublimates said vapors into a crystalline formation, said crystalline formation having a low thermal conductivity.

22. The method of claim 21, wherein said crystalline formation occurs along a defined length of said outer surfaces within said tubular shaft.

23. The method of claim 20, further comprising a step of treating said outer surfaces of said internal tubes to correspond nucleating efficiency with chemical characteristics of said vapors.

* * * * *